United States Patent [19]

Sherman

[11] Patent Number: 5,678,580
[45] Date of Patent: Oct. 21, 1997

[54] DENTAL FLOSS DISPENSER

[76] Inventor: Thomas Mitchell Sherman, 2944 E. Fairmount #211, Phoenix, Ariz. 85016

[21] Appl. No.: 524,602

[22] Filed: Sep. 6, 1995

[51] Int. Cl.$^6$ ................................................. A61C 15/00
[52] U.S. Cl. ............................................. 132/324; 206/63.5
[58] Field of Search .......................................... 132/321, 323, 132/324, 309; 206/63.5, 417, 210, 368

[56] References Cited

U.S. PATENT DOCUMENTS

| 407,362 | 7/1889 | Mason . | |
|---|---|---|---|
| 2,083,398 | 6/1937 | Rohland | 206/61 |
| 3,280,971 | 10/1966 | Regan, Jr. | 206/633 |
| 3,605,765 | 9/1971 | Canby | 132/93 |
| 3,869,044 | 3/1975 | Olsson et al. | 206/63.3 |
| 4,211,330 | 7/1980 | Strock | 206/581 |
| 4,327,755 | 5/1982 | Endelson | 132/92 R |
| 4,881,560 | 11/1989 | Blank et al. | 132/324 |
| 5,074,100 | 12/1991 | Lepie | 132/323 |
| 5,076,423 | 12/1991 | Russack | 206/63.5 |

*Primary Examiner*—Todd E. Manahan
*Attorney, Agent, or Firm*—Richard G. Harrer

[57] ABSTRACT

A dental floss dispenser which, from a size and shape standpoint, looks very much like a credit card housed within a protective case. The dispenser includes a floss holder which can be described as flat, relatively thin, of a generally rectangular shape, and preferably made of a relatively rigid material. The case for the floss holder completely surrounds the holder and is open or openable at one end so that the holder may be easily moved in and out of its case. The case can be made of a flexible plastic material—with a clear plastic being preferred. The holder is provided with a supply of dental floss which is preferably wound from side edge to side edge of the holder and about the middle section thereof. This leaves the upper end of the holder free of floss. Near the upper end of the floss holder which is the end initially withdrawn from the case and on one edge of the holder is a notch which is used to engage and hold the floss after a length has been removed from the holder. A second notch is provided on the opposite edge of the holder and a cutting blade is positioned in this notch to cut the floss. Preferably, the holder is mounted within its protective case in a special manner so that not all of the holder can be removed from the case. That is, stop means are provided in the dispenser which control the distance the holder may be pulled from the case. Such stop means function so that only that end of the holder having the floss engaging notch and the floss cutting means are exposed when the floss holder is pulled from the case. Thus the main portion of the floss, which is wound about the holder, remains covered by the case. This keeps the user's fingers from possibly contaminating the floss and serves to protect the floss from other contamination as well.

18 Claims, 2 Drawing Sheets

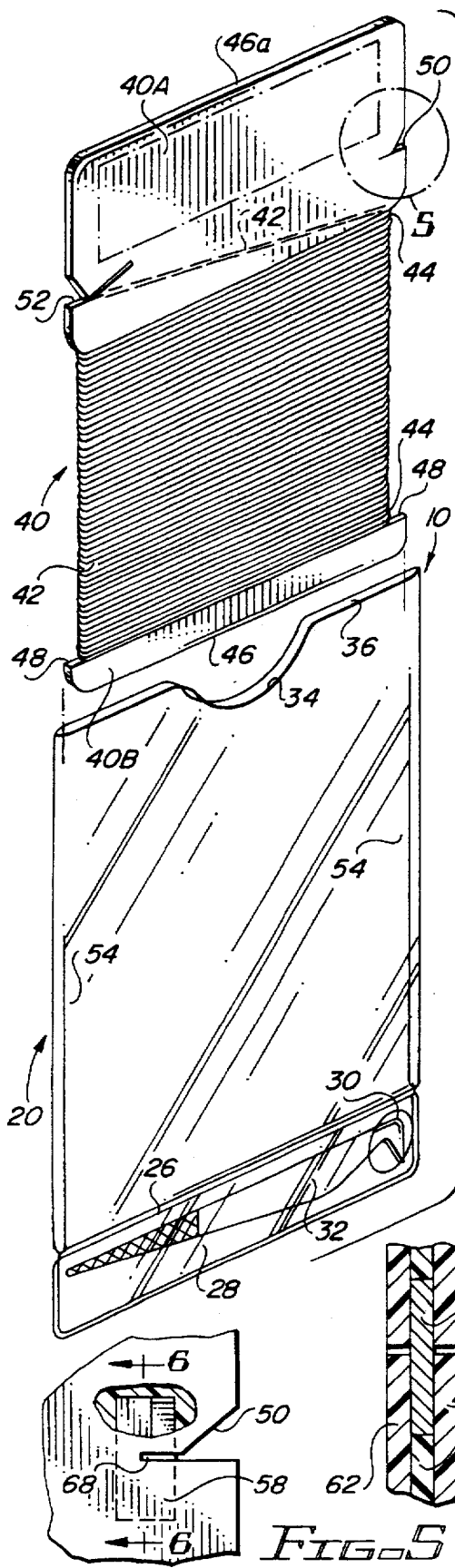

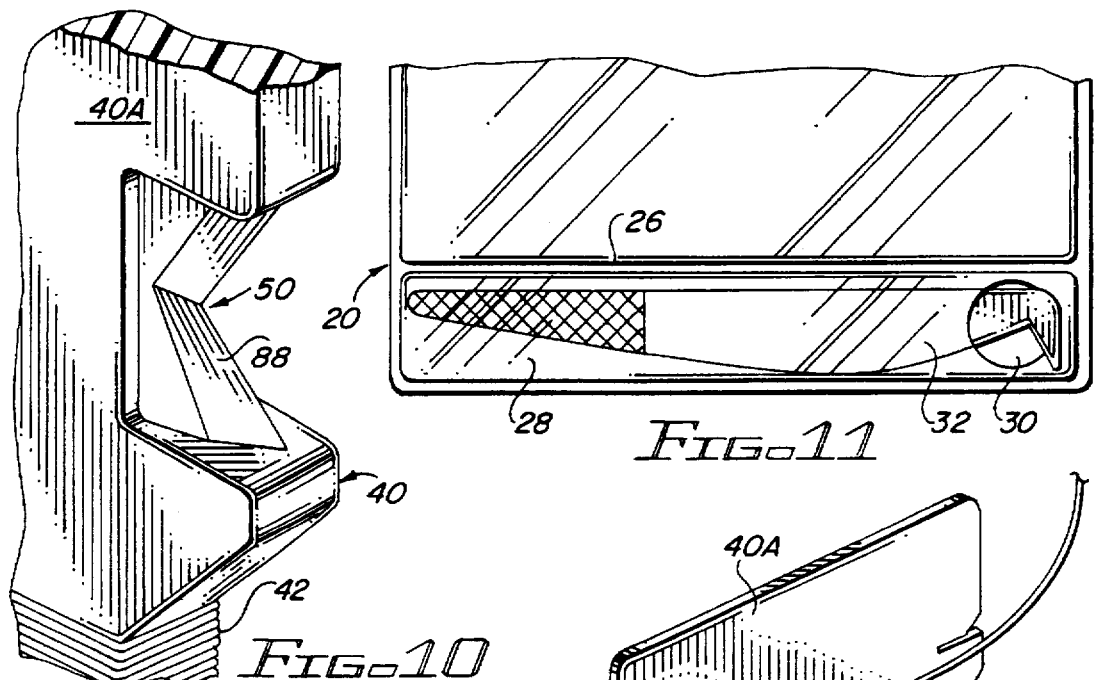
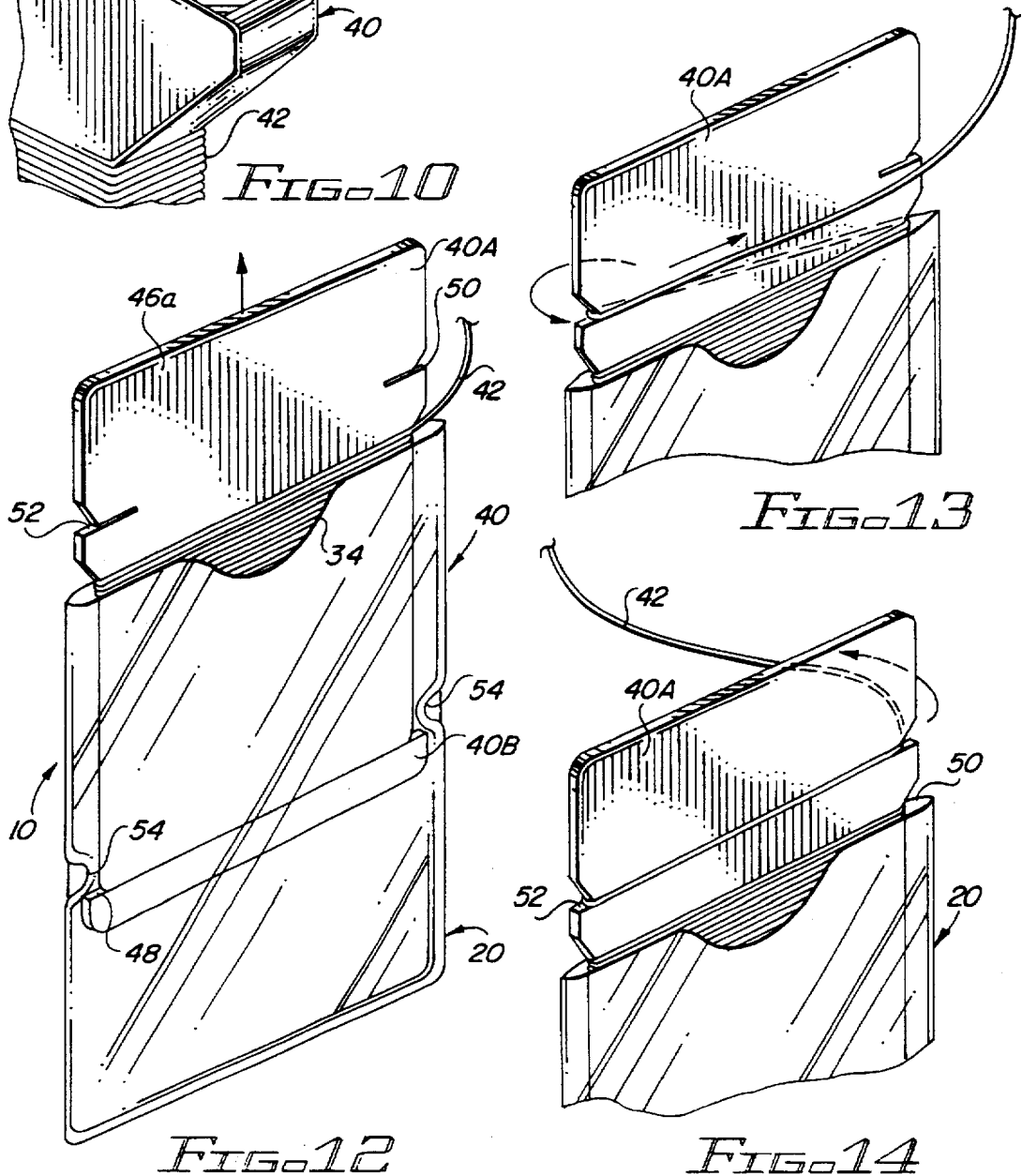

DENTAL FLOSS DISPENSER

FIELD OF THE INVENTION

This invention relates generally to dental floss dispensers, and more particularly to a dispenser which appears much like a credit card in shape and size, making it very easy to carry the dispenser in a wallet or elsewhere on the person.

BACKGROUND OF THE INVENTION

It has been estimated that approximately 90% of Americans are affected by dental disease and that more than one hundred million adult Americans are affected with periodontal disease. It has also been said that in large measure, dental disease is due to the accumulation of bacterial plaque on the teeth. It is this plaque which acts to generate acids, enzymes and other toxins which attack the teeth and gums giving rise to tooth decay and periodontal disease. The value of daily bacterial plaque removal from all 5 tooth surfaces is well established. Food deposits trapped between teeth are not only annoying, but hasten the formation of bacterial plaque.

Since a toothbrush cannot get into the spaces between teeth, it is necessary to use another method. Dental floss is universally recommended by the dental profession for this purpose. Dental floss usually takes the form of a nylon string or other suitable filament of synthetic fiber. Either the waxed or unwaxed type is suitable. The big advantage of dental floss is that it can get into the hard to reach places between the teeth and under bridge work, areas that are otherwise inaccessible to a toothbrush or other dental appliances. Some people utilize toothpicks rather than dental floss for interproximal plaque removal. Toothpicks tend to impact the debris into the crevice between the tooth and gum rather than dislodge it.

Dental floss when used correctly not only removes food particles from between two approximating tooth surfaces but can be extended below the gum tissue along the tooth surface to disrupt and remove the bacterial colonies that grow on that surface. These procedures are necessary at least one time a day to achieve optimum dental health. Debris that lodges between teeth (i.e., strings from celery or meat) is quite an annoyance but is frequently endured due to lack of the availability of a convenient tool for dislodgement. The typical dental floss container or dispenser is not conveniently carried on the person thus making it more difficult for most individuals to follow the dictates of good dental health and comfort. While these dispensers are conveniently stored in the bathroom, an individual who wants to use the floss away from home is faced with the problem of how best to carry a container of floss.

Tarrson U.S. Pat. No. 4,162,688 discloses a dental floss dispenser that is well-known. This dispenser includes a box-like container having a reel of dental floss which is dispensed through a top opening, the container additionally being provided with a cutting blade so that a suitable length of floss may be separated from the reel of floss. Endelson U.S. Pat. Nos. 4,327,755 and 4,881,560 disclose relatively thin dental floss dispensers said to be in a credit card format which allows the dispenser to be carried in a wallet or shirt pocket and the like. The dispenser disclosed in these two patents includes a base panel in which there is a shallow well defined by a peripheral ridge. A supply of floss in flattened form is located in the well with the leading end passing out an aperture in a face panel which is secured to the ridge which defines the well. The floss is severed by a blade which is located in an edge notch formed in the base panel.

SUMMARY OF THE INVENTION

My invention is embodied in a dental floss dispenser which, from a size and shape standpoint, looks very much like a credit card housed within a protective case. The dispenser includes a floss holder which is housed within the protective case, the holder itself looking very much like a credit card. Thus, it can be described as flat, relatively thin, of a generally rectangular shape, and preferably made of a relatively rigid material. The case for the floss holder completely surrounds the holder and is open or openable at one end so that the holder may be easily moved in and out of its case. The case can be made of a flexible plastic material—with a clear plastic being preferred. The clear plastic case permits the user to visually determine the amount of floss remaining on the holder. The holder is provided with an ample supply of dental floss. Preferably the floss is wound from side edge to side edge of the holder and about the middle section thereof. This leaves the upper end of the holder free of floss. Near the upper end of the floss holder which is the end initially withdrawn from the case and on one edge of the holder is a notch which is used to engage and hold the floss after a length has been removed from the holder. A second notch is provided on the opposite edge of the holder and a cutting blade is positioned in this notch to cut the floss. Thus, when a length of floss is needed, the user grasps the end of the end of the holder which is adjacent to the open end of the case, pulls the holder from the case to expose the loose end of the floss and release it from the floss engaging notch. Then the desired amount of floss is removed from the holder, the trailing end of floss is reengaged into the floss engaging notch, passed into the notch having the cutting blade and cut. The exposed end of the holder is then slid back into the protective case or sleeve. Preferably, the holder is mounted within its protective case in a special manner so that not all of the holder can be removed from the case. That is, stop means are provided in the dispenser which control the distance the holder may be pulled from the case. Such stop means function so that only that end of the holder having the floss engaging notch and the floss cutting means are exposed when the floss holder is pulled from the case. Thus the main portion of the floss, which is wound about the holder, remains covered by the case. This keeps the user's fingers from possibly contaminating the floss and serves to protect the floss from other contamination as well. It is a further feature of this invention that a compartment can be provided at one end of the protective case to hold an interproximal plaque removal device or other dental cleaning device.

BRIEF DESCRIPTION OF THE DRAWINGS

FIG. 1 is an exploded perspective view of the floss dispenser;

FIG. 2 is a partial plan view of the dispenser showing one means of retaining a portion of the floss holder within its protective case;

FIG. 3 is an enlarged view of the area "3" of FIG. 2;

FIG. 4 is a plan view of a portion of the dispenser showing another means for retaining a portion of the floss holder within its protective case;

FIG. 5 is a partial plan view of the dispenser showing a notch and cutter blade;

FIG. 6 is a partial cross section taken on the like 5—5 of FIG. 5;

FIG. 7 is a plan view of a piece of metal which has been die cut as the initial step in forming a cutter blade;

FIG. 8 is a partial perspective view of the floss holder showing the mounting of a special cutter blade on the holder;

FIG. 9 is a partial plan view of the floss holder showing the floss cutter blade in place;

FIG. 10 is a partial perspective view of a floss holder showing having a cutter blade formed from the same material used to make the holder;

FIG. 11 is a partial plan view of the protective case showing the compartment for storing a dental cleaning device; and FIGS. 12–14 are partial perspective views of the floss dispenser showing the steps involved in removing floss from the holder and cutting the same.

DETAILED DESCRIPTION OF THE INVENTION

Referring to FIG. 1 there is seen a dental floss dispenser in credit card format and made in accordance with the present invention. The dispenser shown generally at 10 includes a dental floss holder 40 which is contained within a protective case 20. As shown, holder 40 looks much like a credit card in size and thus can be described as flat, relatively thin and generally rectangular in shape and preferably made of a plastic material such as polyvinylchloride, polystyrene and the like. Holder has a top edge 46a bottom edge 46 and opposed side edges. Protective case 20 is sized to accommodate the holder and is preferably made of a clear, relatively flexible plastic material. Case 20 is open at one end 36 and may be provided with a semi-circular shaped cut-out 34 so as to facilitate the user gripping the holder and moving it in and out of its case.

As best shown in FIG. 1, the holder further includes a supply of dental floss 42 which, in the embodiment shown, is wound about the holder in the area designated 44. As seen in FIG. 1, the width of the holder 40 in the area 44 is less than the rest of the holder and it is this narrowed area that receives a supply of the floss 40. As previously noted, it is preferred that the holder 40 is mounted within case 20 in a special manner so that not all of the holder can be removed from its case. That is, stop means are provided which have an important function to control the distance that the holder is permitted to be pulled from its protective case 20. Thus, with the stop means, only the end of the holder having the floss engaging notch 52 and the floss cutter 50 are exposed when the card is partially removed from its case. This means that the floss 42, which is wound about the holder in area 44, is still within the case and covered by the case. This is important in that it keeps the user's fingers and other possible sources of contamination from contacting the dental floss.

The stop means for this special mounting of the holder within its case is shown in FIGS. 1, 2, 3, 4 and 12. This stop means includes means mounted on holder 40 and case 20 which cooperate to control the distance holder 40 may be pulled from the case. As shown in FIGS. 1, 2 and 3, each side edge of case 20 is provided with an arcuate shaped indentation 54 which extends from the edge of case 20 to its interior a relatively short distance. Near the bottom edge 46 of the holder 40 are shoulders 48 which are formed by the reduction in width of the holder in area 44. That is, by reducing the width of the holder in the area 44, shoulders 48 are formed which are the protruding ends of section 40B of the holder. As best shown in FIGS. 2, 3 and 12, when holder 40 is positioned into case 20 so that section 40B is below indentations 54, movement of the holder out of case 20 through opening 36 will be stopped when shoulder 48 makes contact with indentation 54. Thus the position of stop means or indentation 54 on shoulder 48 can be varied so as to regulate the distance which holder 40 can be removed from case 20. As shown best in FIG. 12, indentation 54 and shoulder 48 are positioned so that virtually all of the floss is covered by case 20, although the floss engaging notch 52, cutting notch 50 and a length of floss are exposed.

Another stop means for engaging shoulder 48 is shown in FIG. 4. In this embodiment, the two sides of case 20 are subjected to heat treatment in the area 56 which causes the two sides of case 20 to be "spot welded" together. Although not shown, the same heat sealing technique is applied to the opposite edge of case 20. A further stop means may be formed by applying a small staple or grommet through both the front and back sides of case 20 in the same area as shown for stops 54 and 56.

As shown in FIGS. 5 and 6, a floss cutting means includes a small metal blade 58 anchored in notch 50 such that a small portion of blade 58 overlays the narrowed end 68 of notch 50. As shown best in FIG. 6, blade 58 is embedded between layers 60 and 62 of holder 40. A third layer 64 is provided which is about the same thickness as blade 58 and all three layers are bonded together to form a laminate.

Another floss cutting means 70, which is a feature of this invention, is shown in FIGS. 7–9 inclusive. As shown in FIGS. 8 and 9, metal cutter 70 is mounted on an edge of holder 40 with the cutter itself forming a V-shaped notch or guide 78 for the floss. As shown in FIG. 8, cutter 70 has two generally parallel and opposed sides 84 and 86 which are connected together to form a U-shaped structure with space 82 between the opposed sides. As shown in FIG. 8, it is preferable that the area of holder 40 which is to receive cutter 70 be recessed or routed out so that when cutter 70 is positioned on the holder, each of the sides 84 and 86 lie in the same plane as the surfaces of holder 40. A significant advantage of cutter 70 is that it is relatively easy to mount on holder 40 as compared to the embedding technique employed with respect to blade 58 as shown in FIGS. 5 and 6. Lamination of holder 40 is eliminated when using cutter 70.

To form cutter 70, reference is made to FIG. 7 where a rectangular shaped piece of relatively soft metal 72 is shown having die cuts 74 and 76 which die cuts go completely through the thickness of piece 72. It is preferred that said cuts be beveled so as to create a sharper cutting edge. Each of die cuts 74 and 76 are generally right angles with the vertex of each angle positioned opposite each other and spaced apart to form a a generally square shaped open area 78. The legs of one angle intersect the corresponding legs of the other angle. After piece 72 has been die cut as shown and the rectangular piece has been removed to form open area 78, the piece is bent at its midpoint to give the V-shaped cutter.

In use, a length of floss is introduced into the V-shaped notch 78 of cutter 70. As tension on the floss is increased, the floss is forced into the vertex of notch 78 and then into the extended legs 74a or 76a of die cut angles 74 and 76, which legs have a scissor like effect in cutting the floss.

FIG. 10 shows a further embodiment of the dental floss dispenser which is basically the same as other embodiments previously described except that the cutter 88 is molded or stamped as an integral part of floss holder 40. That is, cutter 88 can be molded from the same plastic used to form holder 40, or, can be stamped from the metal used to form the holder. As shown, the cutting edge of cutter 88 is tapered and V-shaped.

A still further embodiment is shown in FIGS. 1 and 11 wherein a compartment 28 is provided in the case 20 to house an interproximal plaque removal device 32, toothpick or other dental cleaning device. As shown, compartment 28 is a part of case 20 but sealed off from the main portion of the case at 26. Opening 30 is provided at one end of the compartment to allow insertion and removal of the device.

FIGS. 12–14 show the steps involved in using the dental floss dispenser of this invention. As shown in FIG. 12, one wishing to obtain a length of dental floss removes the dental floss dispenser 10 from his/her wallet, pocket, purse or other convenient carrying place and proceeds to remove a portion of floss holder 40 from case 20 by grasping the upper area 40A of the holder in the area exposed by cut-out 34 of case 20. As shown in FIG. 12, the floss holder is moved out of its case a distance, that is, it is removed from the case until shoulder 48 makes contact with arcuate shaped indentation 54 at which point movement of the holder is stopped. As shown in FIG. 12, stop 54 and shoulder 48 are positioned so that virtually all of the floss contained on the floss holder is covered by case 20 with only the floss engaging notch 52, cutting notch 50, and an end of the floss and being exposed.

As shown in FIG. 13, the user then unwinds a length of floss in a counter-clockwise direction from the supply of floss contained in area 44 of holder 40 until a suitable length is obtained. The floss is then engaged in the floss engaging notch 52 and thereafter, as shown in FIG. 14, drawn into the cutting notch 50 where the length of floss is cut. Thereafter, the floss holder is pushed back into the case and the dispenser returned to its carrying place.

From the foregoing it is apparent that the floss dispenser of this invention is both unique and highly versatile. It is truly portable in that its flat design allows it to be easily carried in a pocket, wallet, or purse. Floss is often needed after a meal but is seldom readily available. The dispenser of this invention can always be readily available because it is easily stored or carried with the personal belongings that we normally have with us. The holder itself resembles a plastic credit card with approximate dimensions of 3 inches in length by 2-1/8 inches in width and about 0.040 inches in thickness. The case does not add much to the foregoing dimensions.

Dental practitioners are governed by ethical guide lines relating to advertising and promotion. A significant advantage of this type of dental floss dispenser is that it can be imprinted and personalized with the dentist's name, office location, and a patient appointment reminder. This flat business card format offers extensive advertising opportunity using an ethical oral hygiene product having a high perceived value and a high likelihood of useage and retention by the patient. The dentist provides the product to the patient who uses it and demonstrates it to others, creating referral opportunities and word-of-mouth advertising.

What is claimed is:

1. A dental floss dispenser which, from the a size and shape standpoint, appears much like a credit card housed within a protective case, said dispenser comprising:

(a) a floss holder being generally flat, relatively thin, and of a generally rectangular shape and formed of a relatively rigid material;

(b) a supply of dental floss secured to said holder;

(c) said holder being slideably positioned within a protective case which surrounds said holder, with a portion of said case being open whereby said holder may be pulled a distance out of said case to expose at least a portion of said floss so that a length of floss may be severed therefrom, and thereafter slid back into said case.

2. The dispenser of claim 1 wherein said holder has a top edge, a bottom edge and opposed side edges and wherein said floss is wound about the holder from side edge to side edge and wherein cutting means are mounted on said holder.

3. The dispenser of claim 2 wherein the width of said holder is narrowed in the area around which the floss is wound.

4. The dispenser of claim 2 wherein stop means are provided which means control the distance said holder may be pulled from said case.

5. The dispenser of claim 4 wherein said stop means control the distance that said holder may be pulled from said case so that the floss wound about said holder remains substantially covered by said case when said holder is pulled a distance from said case.

6. The dispenser of claim 5 wherein said stop means comprise means mounted on said holder and on said case which cooperate to control the distance said holder may be pulled from said case.

7. The dispenser of claim 6 wherein the width of said holder is narrowed in the area around which the floss is wound, said narrowed area extending a distance from near the bottom edge of said holder towards the top edge of said holder.

8. The dispenser of claim 7 wherein a shoulder is formed in the holder at the narrowed area of said holder nearest the bottom edge of said holder.

9. The dispenser of claim 8 wherein a stop is provided at a side edge of said case which edge is adjacent to said edge of said holder, said stop being positioned such that when said holder is withdrawn from said case, said shoulder contacts said stop and further movement of said holder from said case is prevented.

10. The dispenser of claim 9 wherein said stop is an indentation extending from an edge of said case a short distance into said case.

11. The dispenser of claim 9 wherein said stop is formed by heat sealing together two opposed sides of said case.

12. The dispenser of claim 9 wherein said stop is formed by stapling together two opposed sides of said case.

13. The dispenser of claim 9 wherein said case is transparent and wherein an edge of that end of said holder which is initially pulled from said case is provided with a floss cutting means and a free end of said floss is exposed when said holder is pulled from said case.

14. The dispenser of claim 13 wherein said holder is also provided with a floss engaging means.

15. The dispenser of claim 13 wherein said case is provided with a separate compartment to house a tooth cleaning device.

16. The dispenser of claim 2 wherein said cutting means are provided along an edge of said holder and is made of the same material as used to form said holder.

17. The dispenser of claim 16 wherein said cutting means is V-shaped and the cutting edge thereof is tapered.

18. The dispenser of claim 17 wherein said holder is made of a relatively rigid plastic material.

* * * * *